United States Patent [19]
Geigel et al.

[11] Patent Number: 4,663,473
[45] Date of Patent: May 5, 1987

[54] ISOCYANATES FROM OXALYL CHLORIDE AND AMINES

[75] Inventors: Maria A. Geigel, Cupertino; Chester W. Marynowski, Mountain View, both of Calif.

[73] Assignee: The United States of America as represented by the Secretary of the Army, Washington, D.C.

[21] Appl. No.: 900,063

[22] Filed: Aug. 25, 1986

[51] Int. Cl.$^4$ ............................................. C07C 71/00
[52] U.S. Cl. ................................................... 560/336
[58] Field of Search ....................................... 560/336

[56] References Cited

U.S. PATENT DOCUMENTS 4,322,365  3/1982  Franzmerger et al. ......... 260/453 P

OTHER PUBLICATIONS

A. J. Speziale and L. R. Smith, J. Org. Chem., 28, 1805 (1963).
J. Goerdeler and H. Schenk, Angew. Chem., 75, 675 (1963).
Ulrich von Gizycki, Angew. Chem. Int. Ed. Engl., 10, 403 (1971).

Primary Examiner—Alan Siegel
Attorney, Agent, or Firm—Jr. Garvin; Freddie M. Bush

[57] ABSTRACT

An isocyanate compound of the general formula $R(NCO)_n$, wherein R is either an aliphatic or an aromatic radical or a combination of both, and n is 1 or a larger integer is prepared by the process comprising dissolving in a high temperature boiling point solvent contained in an agitated, jacketed reactor vessel, an amine of the formula $R(NH_2)_n$, completing a hydrochlorination and precipitation step to form a colloidal suspension of microcrystalline salt particles of amine hydrochloride salt $R(NH_2)_n \cdot nHCl$, introducing oxalyl chloride with agitation and by subsurface injection into the amine hydrochloride salt solution to form an intermediate of amine oxamyl chloride in situ which is thermally decomposed to yield an isocyanate of the general formula $R(NCO)_n$, and separating and purifying the isocyanate by distillation. The unreacted oxalyl chloride and high temperature reaction solvent are recovered by distillation and by absorption from the HCl by-product and are recycled. The by-product HCl is also partially recycled and used for hydrochlorination.

3 Claims, 2 Drawing Figures

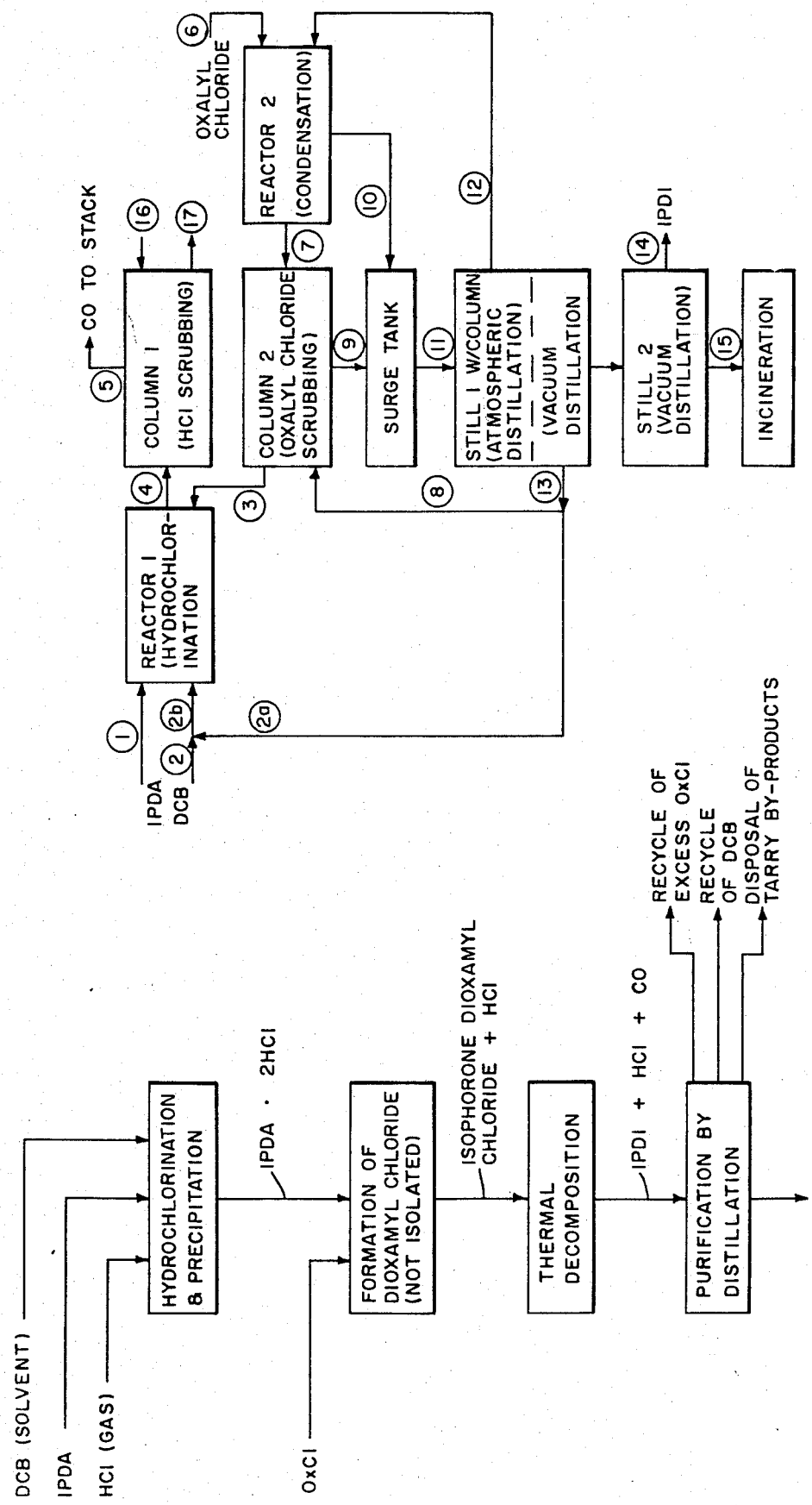

ISOCYANATES FROM OXALYL CHLORIDE AND AMINES

DEDICATORY CLAUSE

The invention described herein was made in the course of or under a contract or subcontract thereunder with the Government and may be manufactured, used, and licensed by or for the Government for governmental purposes without the payment to me of any royalties thereon.

BACKGROUND OF THE INVENTION

Isocyanates are required by the US military as curing agents for hydroxyl-terminated polymers, which are used as binders in many cast-cured solid propellants and plastic-bonded explosives. Several factors are considered in selecting the best isocyanate for the desired application: processability and mechanical properties, pot life and cure rate, toxicity, tendency to hydrolyze, stability and aging, and availability.

3-Isocyanatomethyl-3,5,5-trimethylcyclohexyl isocyanate, commonly known as isophorone diisocyanate (IPDI), excels in most of these categories. Its desirable pot life and cure rate are due to two isocyanate groups with different reactivities, one hindered and the other unhindered. Generally, isocyanates are extremely toxic, but IPDI's lower volatility makes it easier and safer to handle than other candidates. The mechanical and chemical properties imparted by use of IPDI are also good.

Current Process for IPDI Employing a Final Phosgenation Step

IPDI is made from isophorone by the present commerical route shown below. All steps can be accomplished through commercially feasible routes. The final phosgenation step results in high yield, but it presents major problems and capital equipment expenditures because it involves the use of phosgene, an extremely poisonous gas. Only large-scale (millions of pounds a year) production by a continuous process renders a phosgenation route feasible. Indeed, other isocyanates made via phosgenation are available in the United States, but none offers the advantages of IPDI discussed above.

PRESENT COMMERCIAL ROUTE TO IPDI

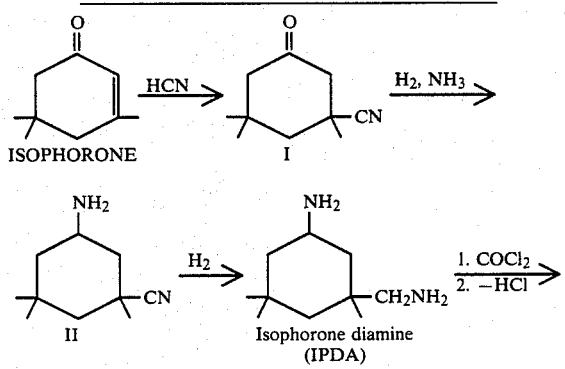

-continued
PRESENT COMMERCIAL ROUTE TO IPDI

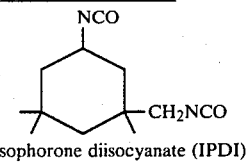

Isophorone diisocyanate (IPDI)

The characteristics of IPDI makes it the choice of curing agents in the isocyanate series; however, because the final step of the present commercial route from IPDA involves the use of phosgene, companies, both foreign and domestic, are reluctant at establishing a US capability because of the current small US military demand for IPDI, because of the strict OSHA and EPA regulations, and because U.S. industrial needs are currently met by Veba-Chemie's production at 3/pound.

Because the interest in processes for preparing isocyanates without phosgene has been an active concern of industry, particularly in recent years as regulations for handling the highly toxic gas have been tightened, much of the current literature available concerns this topic. One such source, U.S. Pat. No. 4,322,365, discloses a method wherein isocyanates are prepared by thermal decomposition of oxalic acid ester amides at not less than 300° C. The oxalic acid amides of the formula R'NHCOCOOR" wherein R' is an aliphatic, cycloaliphatic, ar-aliphatic, aliphatic-aromatic, or aromatic radical and R" is an aliphatic, cycloaliphatic, ar-aliphatic, aliphatic-aromatic, or aromatic radical yield isocyanates which are valuable starting materials for the preparation of crop protection agents, pesticides, dyes, synthetic resins, plastics, textile waterproofing agents, detergents, and adhesives. For further information about this non-phosgene process for preparing isocyanates and uses of same, refer to U.S. Pat. No. 4,322,365 and additional references contained therein.

Compared to the conventional processes, the process of U.S. Pat. No. 4,322,365 is said to "give isocyanates more simply and economically". Also the difficulties with respect to distillation, corrosion problems, and reduced activity of the end products as compared to earlier prior art process, are said to not arise to a significant degree. Additionally, it is an advantage that the process avoids toxic and corrosive chlorocarbonic acid esters, expensive selenuim-catalyzed or noble metal-catalyzed reductible carbonylation of nitro compounds (entailing high pressures, toxic carbon monoxide, and toxic or expensive catalysts), and the involved reaction of amines with dimethyl carbonate (which form numerous by-products).

Although many of the disadvantages of the earlier prior art processes are obviated by the process of U.S. Pat. No. 4,322,365 which employs starting materials prepared by reacting amines with dialkyl oxalates, a one-step process under moderate reaction conditions (80° C.–180° C., less than 2 hours) would be advantageous where optimum energy considerations and the ready availability of starting materials are placed in proper perspective with the process of U.S. Pat. No. 4,322,365. Thus, a one-step process because of energy conservation, not requiring the use of phosgene, and not requiring the starting materials of oxalic acid ester amides which are prepared by reacting amines with dialkyl oxalates which are not readily available, as are the amine hydrochloride salts, is considered to be a superior process.

Therefore, an object of this invention is to provide a one-step process for preparing isocyanates.

A further object of this invention is to provide a one-step process for preparing isocyanates which does not require the use of phosgene.

Still a further object of this invention is to provide a one-step process for preparing isocyanates from oxalyl chloride and amines reacted under moderate reaction conditions in an appropriate high boiling point solvent in the range of 80° C.-180° C.

SUMMARY OF THE INVENTION

The process of this invention for preparing isocyanates is a one-step process comprising heating an amine or an amine hydrochloride salt with excess oxalyl chloride (OxCl) in a high boiling point solvent from about 80° C.-180° C. for a reaction time of about 0.5-2 hours.

An appropriate high boiling point solvent is selected from o-dichlorobenzene (DCB) and decahydronaphthalene (Decalin).

After forming the isocyanate, the excess oxalyl chloride and solvent are removed and the isocyanate is separated and purified by distillation.

The brief description of the process employing isophorone diamine (IPDA) as the amine reactant is as follows:

IPDA is dissolved in DCB, and dry hydrogen chloride (HCl) gas in excess is bubbled through in an agitated, jacketed reactor. The excess HCl passes through the reflux condenser, dry ice traps, oil bubbler, and liquid backup trap, and is absorbed in a water scrubber.

OxCl (3 times theoretical) is added to the IPDA-dihydrochloride salt mixture, and the temperature is brought up to the final target value (in the range of 80°-180° C.) over a period of 0.5 to 2 hour. An unstable intermediate is formed and is immediately thermally decomposed to form IPDI plus carbon monoxide (CO) and HCl. The excess OxCl is promptly removed by distillation at 130° C.

About two-thirds of the DCB solvent is next removed by vacuum distillation. The residual solution of IPDI in DCB is transferred to a smaller vacuum distillation apparatus for final purification.

BRIEF DESCRIPTION OF THE DRAWINGS

A block flow diagram for isophorone diamine (IPDA) conversion to isophorone diiscocyanate (IPDI) by the oxalyl chloride (OxCl) route, and using o-dichlorobenzene (DCB) as solvent, is depicted in FIG. 1 of the drawing.

FIG. 2 of the drawing depicts a block diagram of a projected commercial scale IPDI synthesis including flow streams by the oxalyl chloride route.

DESCRIPTION OF THE PREFERRED EMBODIMENT

The one-step process of this invention for preparing isocyanates comprises reacting an amine or an amine hydrochloride salt with excess oxalyl chloride in a solvent selected from o-dichlorobenzene and decahydronaphthalene at a temperature from about 80° C.-180° C. for 0.5-2 hours. Excess oxalyl chloride and solvent are removed and the isocyanate is separated and purified by distillation.

The oxalyl radical —CO.CO— of oxalyl chloride COCl.COCl (OxCl) reacts with isophrone diamine hydrochloride salt (IPDA.2HCl) to form the intermediate isophorone dioxamyl chloride which subsequently is thermally decomposed to yield isophorone diisocyanate (IPDI). The overall reaction process is represented by the equation*:

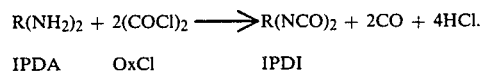

$$R(NH_2)_2 + 2(COCl)_2 \longrightarrow R(NCO)_2 + 2CO + 4HCl.$$

IPDA      OxCl      IPDI

* For simplification the hydrochlorination and precipitation step and formation of dioxamyl chloride are not shown.

The block diagram shown in FIG. 1 of the drawings depicts the process of this invention for preparing isophorone diisocyanate. This process for preparing isophorone diisocyanate (IPDI) comprises dissolving IPDA in the high boiling point solvent o-dichlorobenzene (DCB) and bubbling dry HCl gas into the solution in excess to achieve hydrochlorination and precipitation. Oxalyl chloride (OxCl) (preferably 3 times theoretical) is added to the IPDA dihydrochloride salt (IPDA.2HCl) mixture, and the temperature is brought up to the final target value (in the range of 80° C.-180° C.) over a period of 0.5 to 2 hour. An unstable intermediate, isophorone dioxamyl chloride, undergoes thermal decomposition to yield IPDI+HCl+CO. IPDI is purified and separated by distillation. The excess OxCl is recycled, the DCB is recycled and the remaining tarry by-products are removed from the reactor system.

Table I below sets forth optimization experiments performed to establish combinations for the preferred embodiments.

TABLE I

OPTIMIZATION EXPERIMENTS ON OXALYL CHLORIDE ROUTE

| Run | Scale[a] (g) | Salt or Amine | OxCl (eq.) | Maximum Temperature (°C.) Oil Bath | Maximum Temperature (°C.) Reaction | Run Time (hr) | IPDI Yield[b] (%) | Comments |
|---|---|---|---|---|---|---|---|---|
| 1[c] | 1 | Salt | 1.1 | 180 | — | 24.0 | 22 | Hot addition[d] |
| 2[c] | 15 | Salt | 2 | 180 | — | 1.5 | 49 | Hot,[d] slow addition (20 min) |
| 3[c] | 1 | Salt | 3 | 180 | — | 1.5 | 70 | Hot addition[d] |
| 4 | 100 | Salt | 3 | 180 | — | 1.5 | <1 | Hot,[d] slow addition (120 min) |
| 5 | 50 | Salt | 3 | 160–180 | — | 1.5 | 12 | Hot,[d] slow addition (60 min) |
| 6 | 1 | Salt | 1.1 | 180 | — | 1.0 | 5 | — |
| 7 | 1 | Salt | 3 | 180 | — | 1.5 | 56 | Hot addition[d] |
| 8 | 1 | Salt | 3 | 180 | — | 2.0 | 62 | — |
| 9 | 1 | Amine | 3 | 180 | — | 1.5 | 55 | — |
| 10 | 0 | Amine | 3 | 160 | — | 2.0 | 38 | — |
| 11 | 10 | Amine | 3 | 180 | — | 1.5 | 30 | — |
| 12 | 10 | Amine | 3 | 180 | — | 1.5 | 28 | All reagents distilled |
| 13 | 1 | Salt | 3 | 180 | — | 2.0 | 14 | Old OxCl |
| 14 | 1 | Amine | 3 | 180 | — | 2.0 | 3.5 | Old OxCl |
| 15 | 1 | Amine | 3 | 180 | — | 1.5 | 10 | Distilled OxCl |

TABLE I-continued
OPTIMIZATION EXPERIMENTS ON OXALYL CHLORIDE ROUTE

| Run | Scale[a] (g) | Salt or Amine | OxCl (eq.) | Maximum Temperature (°C.) Oil Bath | Maximum Temperature (°C.) Reaction | Run Time (hr) | IPDI Yield[b] (%) | Comments |
|---|---|---|---|---|---|---|---|---|
| 16 | 1 | Salt | 3 | 180 | — | 4.0 | 83 | Old OxCl, new GC column |
| 17 | 1 | Amine | 3 | 180 | — | 4.0 | 40 | — |
| 18 | 10 | Salt | 3 | 168–180 | — | 2.0 | 55 | In presence of stainless steel |
| 19 | 1 | Salt | 3 | 180 | — | 2.0 | 80+ | Old OxCl |
| 20 | 1 | Salt | 3 | 130 | — | 2.0 | 62 | Temperature study |
| 21 | 1 | Salt | 3 | 155 | — | 2.0 | 63 | Temperature study |
| 22 | 1 | Salt | 3 | 200 | — | 1.5 | 48 | Temperature study |
| 23 | 10 | Salt | 3 | 200 | 176 | 2.5 | 40 | Control |
| 24 | 10 | Salt | 6 | 190 | 100–120 | 3.0 | 35 | Excess OxCl lowered reaction temperature |
| 25 | 10 | Salt | 3 | — | 180 | 1.0 | 14.5 | Reaction in autoclave; sprang leak at 1 hr |
| 26 | 10 | Salt | 3 | — | 180 | 2.5 | 7 | Reaction in autoclave; pressure reached 400 psi |
| 27 | 10 | Salt | 3 | 193 | 174 | 1.5 | 49 | Condenser on stirrer to prevent loss of OxCl |
| 28 | 1 | Salt | 3 | 180 | — | 1.5 | 28 | Alternative, less toxic solvent (decaline)[e] |
| 29 | 45 | Salt | 3 | — | 165 | 1.5 | 46.9 | "Tight" glassware; 45.77% (18.8 g) isolated crude yield |
| 30 | 50 | Salt | 3 | — | 162 | 1.0 | 43 | Salt made in situ; "tight" glassware; 45.5% (22.8 g) crude yield |
| 31 | 100 | Salt | 3 | — | 156 | 2.0 | 50 | Condenser held at −5° C.; exhaust gases trapped; "tight" glassare; 38.7% |
| 32 | 100 | Salt | 3 | — | 148 | 1.5 | 43.5 | Condenser held at −5° C.; exhaust gases trapped; "tight" glassware; 32.0% (29.1 g) isolated crude yield |
| 33 | 42 | Salt | 3 | — | 168 | 1.25 | 36 | 41% (15.7 g) isolated crude yield |
| 34 | 20 | Salt[f] | 3 | — | 80 | 31.0 | 34 | Material balance study; atempt to favor intermediate formation; held at 40° C. for 4 hrs, at 60° C. for 8 hrs |
| 35 | 10 | Salt | 3 | — | 167 | 7.75 | 32 | High-dilution reaction, yield peaked at 5 hr |
| 36 | 7 | Amine | 3 | — | 157 | 29.0 | 40 | Looked for intermediate formation in solution; held at 40° C. for 27 hr, then heated to maximum temperature |
| 37 | 1 | Amine | 3 | — | 175 | 1.5 | <6 | Mixed IPDA and OxCl neat, then heated solid in solvent to temperature; yield unknown because purity of solid unknown; fast injection of refluxed OxCl |
| 38 | 1 | Salt | 3 | 180 | 164 | 1.0 | 88 | Temperature study at 1-g scale |
| 39 | 1 | — | 3 | 180 | 175 | 6.0 | 100 10 | Demonstrates decomposition of IPDI heated in solution presence of OxCl |
| 40 | 7 | Amine | 3 | 180 | — | 1.0 | 4 | Hot tube reaction (very low yield; mechanical problem) |
| 41 | 1 | Salt | 3 | 130 | 126 | 3.0 | 70 | Temperature study at 1-g scale |
| 42 | 1 | Salt | 3 | 155 | 154 | 2.5 | 66 | Temperature study at 1-g scale |
| 43 | 1 | Salt | 3 | 200 | 164 | 1.5 | 40 | Temperature study at 1-g scale |
| 44 | 8.5 | Salt | 3 | —[g] | 168 | 1.5 | 78 | New Adapter (subsurface injection of refluxed OxCl) |
| 45 | 10 | Salt[f] | 3 | —[g] | 165 | 1.5 | 55 | Same as Run 44, except with in situ salt |
| 46 | 10 | OLS[h] | 2 | — | 165 | 2.3 | 7 | Unsuccessful run; bad batch of off-line salt |
| 47 | 10 | OLS[h] | 2 | — | 165 | 0.5 | 1 | Unsuccessful run; bad batch of off-line salt |
| 48 | 10 | OLS[h] | 2 | — | 167 | 1.5 | 68 | New batch of off-line salt; 2 eq. OxCl gives lower yield than 3 eq. |
| 49 | 10 | OLS[h] | 3 | — | 165 | 1.5 | 78 | Repeat of Run 44 for reproducibility (good check) |
| 50 | 10 | Salt[f] | 3 | — | 160 | 1.25 | 45 | In situ salt formed and isolated, then reacted |
| 52 | 10 | OLS[g] Salt | 3 | — | 165 | 1.6 | 70 | OxCl removed after peak (40 min) to slow degradation of IPDI |
| 53 | 10 | Salt[f] Salt | 3 | — | 150 | 1.5 | 45 | OxCl removed after peak (30 min) to slow degradation of IPDI |
| 54 | 10 | Salt[f] Salt | 3 | — | 130 | 1.6 | 72 | Lower temperature increases yield with in situ salt (compare Run 51) |
| 55 | 10 | Salt[f] | 3 | — | 110 | 1.5 | 49 | Temperature study; (in situ salt analyzed as 72% disalt) |
| 56 | 10 | Salt[f] | 3 | — | 110 | 1.5 | 49 | Temperature study; (in situ salt analyzed as 76% disalt) [wet] |
| 57 | 10 | OLF[g] | 3 | — | 165 | 1.5 | 44 | Run at 10% IPDI solution, to complete concentration study |
| 58 | 10 | Salt[f] | 3 | — | 130 | 1.5 | 60 | OxCl removal after peak in IPDI yield with no loss of yield; (in situ salt analyzed at 90% disalt [wet]) |

TABLE I-continued
OPTIMIZATION EXPERIMENTS ON OXALYL CHLORIDE ROUTE

| Run | Scale[a] (g) | Salt or Amine | OxCl (eq.) | Maximum Temperature (°C.) Oil Bath | Maximum Temperature (°C.) Reaction | Run Time (hr) | IPDI Yield[b] (%) | Comments |
|---|---|---|---|---|---|---|---|---|
| 59 | 10 | Salt[f] | 3 | — | 130 | 2.0 | 55 | OxCl addition took 5 min, OxCl removal after peak in IPDI yield, with little loss in yield; (in situ salt analyzed as 88% disalt [wet]) |
| 60 | 10 | Salt[f] | 3 | — | 165 | 1.3 | 0 | Salt formed in MeOH, o-DCB added, salt precipitated as MeOH was distilled off; no IPDI was formed. |

[a]Weight of IPDA or salt charged.
[b]Based on GC analysis.
[c]These runs used reagent grade (99%) OxCl; all other runs used commerical (98%) OxCl.
[d]Hot: OxCl added to reaction mixtures at ~160° C.; cold: OxCl added at 25° C. and then heated temperature.
[e]All other runs used DCB solvent.
[f]In situ.
[g]Electric heating mantle.
[h]Off-line salt.

Table II below shows the criticality of providing excess equivalents of oxalyl chloride for higher yields of isophorone diisocyanate (IPDI).

TABLE II
Effect of Excess Oxalyl Chloride on Yield of IPDI

| Equivalents of Oxalyl Chloride | IPDI Yield Percent* |
|---|---|
| 1.1 | 22 |
| 2.0 | 45 |
| 3.0 | 79 |

*at 180° C. in o-dichlorobenzene (o-DCB) solvent for 1 hour; yield is based on IPDA charged.

Subsequent pilot plant scale runs showed that, with good agitation and efficient physical contact, a temperature of about 90° C. is optimal for rapid conversion of the in situ salt to give IPDI yields in excess of 80%. An important process feature for effecting efficient contact between the refluxed oxalyl chloride and the IPDA hydrochloride relates to subsurface injection of refluxed oxalyl chloride to prevent boil off again of the oxalyl chloride prior to chance for reaction.

Production Process Description

The procedure envisioned for a commercial scale production facility is described below in sequence and is conveniently illustrated in FIG. 2 for easy reference. IPDA is dissolved in o-DCB, and dry hydrogen chloride gas in excess is passed therein in an agitated, jacketed reactor. The excess HCl and CO (originating from the recycled incoming hydrogen chloride gas, see below) is passed to a scrubber and is scrubbed by dilute caustic soda. The final CO gas is vented.

The IPDA-dihydrochloride salt in o-DCB in the reactor is heated up, and oxalyl chloride is added. The heating is continued at a selected temperature in the range of 80° C. to 180° C., IPDI is thus formed, releasing HCl and CO. This gas contains oxalyl chloride. Before this gas can be used for making IPDA-hydrochloride, the oxalyl chloride has to be removed. This is achieved by passing it through an absorption column in contact with o-DCB. This scrubbed gas is then used for hydrochlorination.

A whole batch, starting from charging of IPDA to the discharge of IPDI solution, takes 4 hours. Two reactors are provided as shown in production relationship in FIG. 2. When one reactor is in hydrochlorination, the other reactor is in reaction with oxalyl chloride. The HCl gas stream from one reactor is used in the other reactor. Only at start-up does one have to add fresh HCl. All together, 12 batches are made in a 24-h calendar day.

The reaction product from the reactor is a solution of IPDI and excess unused oxalyl chloride in o-DCB. This solution is discharged to a surge tank. The o-DCB/oxalyl chloride solution from scrubbing of the HCl/CO gas is also added to the surge tank. When 12 batches have been collected, the whole content is discharged to a batch still. There it is first distilled at atmospheric pressure to recover the excess oxalyl chloride as distillate and then vacuum distilled at 20 mm Hg to recover o-DCB. After vacuum distillation removal of IPDI, the final still bottoms (containing tars and polychlorinated biphenyl, PCBs) are collected for incineration. The expected yield of IPDI is 78%, based on IPDA consumed.

Because this operation is projected to be attached to an existing plant, the small amount of still bottoms may be incinerated together with other solid waste in a presumably existing incinerator. If there is none, or it is not suitable for incinerating the waste from this process, a small incinerator has to be provided. The gas from the incinerator should pass to the HCl scrubber before discharging to a stack.

At a projected capacity of only 20,000 lb/yr., a fully continuous operation is not practical. However, a conventional batch process would need storage of HCl gas and there would be more likelihood of leakage of gas containing toxic oxalyl chloride in connection with start-up and shut-down of batches. The present design, while still a batch operation, minimizes the above disadvantages by venting all vessels to each other or to gas scrubbers.

Table III hereinbelow depicts calculated stream flows and compositions for IPDI synthesis by oxalyl chloride route and reaction products related thereto. The numbers above the columns correspond to the stream numbers circled and shown in FIG. 2.

TABLE III

CALCULATED STREAM FLOWS AND COMPOSITIONS FOR IPDI SYNTHESIS BY OxCl ROUTE

| Compn | Mol Wt | \multicolumn{19}{c}{Stream Components (lb/batch*)} |
|---|---|---|---|---|---|---|---|---|---|---|---|---|---|---|---|---|---|---|---|---|

| Compn | Mol Wt | 1 | 2 | 2a | 2b | 3 | 4 | 5 | 6 | 7 | 8 | 9 | 10 | 11 | 12 | 13 | 14 | 15 | 16 | 17 |
|---|---|---|---|---|---|---|---|---|---|---|---|---|---|---|---|---|---|---|---|---|
| IPDA | 170.3 | 4.3 | — | — | — | — | — | — | — | — | — | — | — | — | — | — | — | — | — | — |
| O—DCB | 147. | — | 0.3 | 55.7 | 56 | — | — | — | — | — | 10 | 10 | 56. | 792 | — | 788 | — | — | — | — |
| HCL | 36.5 | — | — | — | — | 3.6 | 1.8 | — | — | 3.6 | — | — | — | — | — | — | — | — | — | — |
| Oxalyl chloride | 127. | — | — | — | — | — | trace | — | 7.1 | 0.3 | — | 0.3 | 0.4 | 8.4 | 8.3 | — | — | — | — | — |
| CO | 28. | — | — | — | — | 1.4 | 1.4 | 1.4 | — | 1.4 | — | — | — | — | — | — | — | — | — | — |
| IPDI | 220.3 | — | — | — | — | — | — | — | — | — | — | — | 5 | — | — | — | — | 60 | — | — |
| Heavy ends | — | — | — | — | — | — | — | — | — | — | — | — | — | — | — | — | — | 7 | — | — |
| NaOH | 40. | — | — | — | — | — | — | — | — | — | — | — | — | — | — | — | — | — | 30 | 7 |
| NaCl | 58.5 | — | — | — | — | — | — | — | — | — | — | — | — | — | — | — | — | — | — | 34.7 |
| Water | 18. | — | — | — | — | — | — | — | — | — | — | — | — | — | — | — | — | — | 234 | 234 |

*Streams (1)–(10): 12 batches per 24-h day.
Streams (11)–(15): 1 batch per 24-h day.
Streams (16)–(17): average continuous rate per 24-h day.
The tabulated stream flows represent 330 days/yr operation on IPDI; to convert to operation for 5 days/yr, multiply each entry by 66.

In further reference to FIG. 2 of the drawing, the flow process of this invention is depicted for a 2 reactor system. Hydrochlorination and condensation occur in sequence for each reactor. When one reactor is in hydrochlorination, the other is in condensation, and vice-versa. The production batches illustrated in Table III, and employing the circled streams of operations shown in FIG. 2 of the drawing, are further explained in the footnotes of Table III. For example, streams 1–10 are employed for each of 12 batches per 24 hour day, streams 11–15 are employed once per 24 hour day, and streams 16–17 show average continuous rate per 24 hour day.

Recycle of excess oxalyl chloride and the reaction solvent is achieved by separating and scrubbing to remove reaction gases HCl and CO for recovery. Any excess oxalyl chloride contained in the HCl must be removed before this gas can be used for making IPDA-hydrochloride. This can be achieved by passing it through an absorption column in communication with the reaction solvent.

We claim:

1. A process for preparing isocyanate compounds having the general formula $R(NCO)_n$, where n is 1 or a larger integer, said process comprising completing the steps of:

(i) dissolving an amine of the formula $R(NH_2)_n$, wherein R is either an aliphatic or an aromatic radical, or a combination thereof, in a high temperature boiling point reaction solvent contained in an agitated, jacketed reactor vessel, said high temperature boiling point reaction solvent selected from o-dichlorobenzene and decahydronaphthalene;

(ii) bubbling an excess of dry hydrogen chloride gas into said amine solution to complete a hydrochlorination and precipitation step to form a colloidal suspension of microcrystalline salt particles of the amine hydrochloride salt $R(NH_2)_n \cdot nHCl$;

(iii) heating said amine hydrochloride salt in said solvent to about 90° C. and introducing oxalyl chloride into said amine hydrochloride salt solution with agitation and by subsurface injection in an excess equivalent amount and forming an amine oxamyl chloride $R(NHCOCOCl)_n$, $+HCl$;

(iv) continue heating said amine oxamyl chloride within the temperature range of about 90° C. to about 180° C. for a time period of from about 0.5 to about 2 hours to achieve thermal decomposition of said amine oxamyl chloride to thereby form an isocyanate compound of the general formula $R(NCO)_n$;

(v) separating said isocyanate compound from excess oxalyl chloride, said solvent, and tarry reaction products formed in said reactor vessel;

(vi) recovering said oxalyl chloride and said solvent for recycling and completing scrubbing procedures to remove reaction gases from said oxalyl chloride and said solvent prior to recycling; and, (vii) purifying said separated isocyanate compound by distillation.

2. The process as claimed in claim 1 for preparing a diisocyanate compound having the general formula $R(NCO)_2$ wherein said amine is isophorone diamine and said R of said amine is the combined aromatic-aliphatic radical:

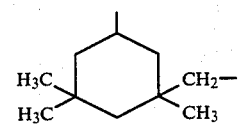

and wherein said diisocyanate formed and separated is isophorone diisocyanate having the formula:

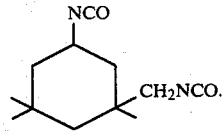

3. The process as claimed in claim 2 wherein said excess equivalent weight of oxalyl chloride is three times theoretical.

* * * * *